United States Patent
Diaz et al.

(10) Patent No.: US 8,324,894 B2
(45) Date of Patent: Dec. 4, 2012

(54) RESONANT LINEARLY POLARIZED EDDY CURRENT SENSOR

(75) Inventors: Rodolfo E. Diaz, Phoeniz, AZ (US); Jeffrey W. Peebles, Phoenix, AZ (US); Richard LeBaron, Chandler, AZ (US); Richard Ormeno, Baltimore, MD (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 440 days.

(21) Appl. No.: 12/520,809

(22) PCT Filed: Dec. 20, 2007

(86) PCT No.: PCT/US2007/026282
§ 371 (c)(1),
(2), (4) Date: Jul. 7, 2009

(87) PCT Pub. No.: WO2008/079391
PCT Pub. Date: Jul. 3, 2008

(65) Prior Publication Data
US 2009/0302834 A1    Dec. 10, 2009

Related U.S. Application Data

(60) Provisional application No. 60/871,525, filed on Dec. 22, 2006.

(51) Int. Cl.
*G01N 27/72* (2006.01)
(52) U.S. Cl. .................. 324/239; 324/233; 324/240
(58) Field of Classification Search .......... 324/228–243
See application file for complete search history.

(56) References Cited

U.S. PATENT DOCUMENTS

| | | | | |
|---|---|---|---|---|
| 3,618,103 A | * | 11/1971 | Ringland | 343/727 |
| 4,940,992 A | * | 7/1990 | Nguyen et al. | 343/803 |
| 5,381,093 A | * | 1/1995 | Kawamoto | 324/318 |
| 6,703,830 B2 | | 3/2004 | Kaste | |
| 7,242,186 B2 | | 7/2007 | Zimmermann | |

(Continued)

FOREIGN PATENT DOCUMENTS

JP        11002647        1/1999

(Continued)

OTHER PUBLICATIONS

International Search Report and Written Opinion dated May 23, 2008 for PCT/US2007/026282 (10 pages).

*Primary Examiner* — Huy Q Phan
*Assistant Examiner* — Temilade S Rhodes-Vivour
(74) *Attorney, Agent, or Firm* — Fish & Richardson P.C.

(57) ABSTRACT

A linearly polarized eddy current sensor including a source antenna and a parasitic antenna coupled to the source antenna, serves as a high sensitivity tool for the measurement of the surface impedance of sheet goods without requiring contact with the sample. Sheet goods can have an anisotropic, frequency-dependent surface impedance that is sensitive to minor changes in configuration of the sample. Because the electric field induced by the sensor is linearly polarized, measurement of directionally dependent sheet impedance can be achieved. The measurement is performed with the resonant device operating in resonance mode whereby the immediate proximity of the material to be measured causes damping and shifting of the coupled loop resonance. The resonant frequency of the sensor can be tuned by making changes to its geometry.

24 Claims, 8 Drawing Sheets

U.S. PATENT DOCUMENTS

2002/0163333 A1* 11/2002 Schlicker et al. ............. 324/242
2003/0214437 A1* 11/2003 Rawnick et al. ....... 343/700 MS
2004/0189380 A1* 9/2004 Myer et al. ................ 330/124 R
2005/0171703 A1* 8/2005 Goldfine et al. ................ 702/30
2006/0132123 A1* 6/2006 Wang et al. ................... 324/239
2008/0150148 A1* 6/2008 Frey et al. .................... 257/769

FOREIGN PATENT DOCUMENTS

| JP | 2005049229 | 2/2005 |
| KR | 1020000033216 | 6/2000 |
| WO | WO 2008/079391 | 7/2008 |

\* cited by examiner

RESONANT LINEARLY POLARIZED EDDY CURRENT SENSOR

CROSS-REFERENCE TO RELATED APPLICATIONS

This application is a national stage application of and claims the benefit of PCT Application No. PCT/US2007/026282, filed on Dec. 20, 2007, and published as WO 2008/079391, which claims priority to U.S. Provisional Application No. 60/871,525, filed on Dec. 22, 2006. The disclosure of the two prior applications are considered part of (and incorporated by reference in) the disclosure of this application.

FIELD

Radio frequency (RF) and microwave sensors are generally discussed herein, with particularly discussions extended to a sensor for measurement of sheet impedance.

BACKGROUND

Resistive sheet goods generally include an organic film (polymer or paper) to which has been affixed a thin electrically conducting layer. Such materials can be applied to heating elements, resistive loads in flexible circuits, resistive terminations for antennas, and resistive components of composite materials for absorption of electromagnetic waves. In the latter category, these films are known as R-cards and are integral parts of Salisbury Screens, Jaumann absorbers and lossy Honeycomb. Controlling the surface resistance, measured in ohms per square ($\Omega/\square$) is critical for these applications both in terms of its precise value and its variation during the manufacturing process. Therefore, methods for the measurement of such properties are important both in a controlled laboratory environment as well as on the production floor. Precise determination of the surface resistance is the desired application in laboratory instruments, whereas relative determination of the same, say in comparison to a calibration standard, is frequently the critical application in a production environment.

In a laboratory environment, careful placement of the sheet may be an acceptable requirement for attaining high levels of accuracy and the time to perform the measurement is not necessarily critical. However, in a production environment the sheet goods may be moving as fast as 100 feet per minute past the sensor. Thus, it is clear that the details of the measurement set-up and the data reduction algorithms may differ depending on the application.

Depending on the manufacturing process and the organic substrate used, the sheet goods' surface resistance may be direction dependent. That is, the sheet resistance in the "down web" and "cross web" directions may differ. This anisotropy may be unintentional and as high as a ratio of 3 to 1, or it could be designed into the sheet by the use of imprinted geometric patterns and be as high as 10 to 1. The subsequent application of anisotropic sheets to a finished product such as a composite material may take advantage of this anisotropy to yield a highly anisotropic product or average it out to result in a net isotropic product. In the former case, accurate measurement of the anisotropy ratio in the sheets may be critical, whereas in the later case it is the average direction-independent resistance that matters. Thus, surface resistance measurement sensors able to measure both direction-specific and direction-averaged sheet resistance values are desired.

Although destructive measurement methods can be used, a non-destructive measurement method is generally desired. In principle, a small square sample of a resistive sheet could be cut, two opposing edges connected to electrodes and the resulting complex current measured under an applied alternating voltage. However, such an approach is slow, wasteful and highly undesirable for profitable manufacturing. Furthermore, many materials of interest are manufactured by processes that leave a disconnected network of conducting material on the film. Such a coating is strongly frequency dependent and may register as an open circuit at DC while appearing highly conductive at microwave frequencies. The prior art approach just described of measuring a small square sheet sample will not necessarily accurately represent the response of the sheet to electromagnetic waves in the microwave range. This is because the electric field in the test set-up described is essentially quasi-electrostatic by nature and thus easily distorted by other nearby high permittivity structures. To measure the frequency dependent conductance of a sheet in such a set-up would require guaranteeing that the electric flux density is always guided by the sheet from electrode to electrode. This is nearly impossible to guarantee.

SUMMARY

An aspect of an embodiment of the present invention provides a sensor capable of quickly measuring surface impedance characteristics of a sample without requiring destruction of or contact with the sample.

An embodiment of the present invention includes an eddy current sensor having a source antenna with two sub-loops that are substantially symmetrical with respect to an imaginary line between the two sub-loops. The source antenna is adapted to generate a magnetic quadrupole when electric currents circulate on the two sub-loops in opposing directions. The source antenna is also adapted to induce a substantially linearly polarized electric field in a region between the two sub-loops. The eddy current sensor may further be coupled with a parasitic device, and the parasitic device may have a similar construction to that of the source antenna.

A further embodiment of the present invention forms the two sub-loops of the source antenna with a loop conductor and a two-conductor transmission line. The loop conductor is bisected by an imaginary line crossing the loop conductor at a first point and a second point. The transmission line crosses the first point such that the first conductor is electrically coupled with the loop conductor, and extends along the imaginary line toward the inside of the loop conductor, ending at a third point on the imaginary line. The second conductor of the transmission line does not contact the loop conductor at the first point, but extends along the imaginary line, past the third point, and is electrically coupled with the loop conductor at the second point.

In a further embodiment of the present invention, the loop conductor has an annular shape, and the transmission line is a coaxial conductor, with the first conductor being the outer conductor, and the second conductor being the inner conductor of the coaxial conductor.

Another embodiment of the present invention is a method for measuring a sheet impedance of a sample, by driving two substantially symmetrical circulating currents circulating in opposing directions on a compound loop structure comprising two sub-loops, to result in a magnetic quadrupole. The magnetic field of the magnetic quadrupole is varied over time to induce an electric field in a region between the two current loops. The sensor detects changes in the electromagnetic field caused by currents in the sample driven by the induced electric field.

A further embodiment couples the compound loop structure with a parasitic compound loop structure to increase a quality factor of the compound loop structure. The parasitic compound loop structure may comprise an open circuited transmission line, and the resonance frequency of the compound loop structure may be tuned by controlling a length of the open circuited transmission line. The sensitivity of the sensor may be controlled by controlling a distance between the compound loop structure and the parasitic compound loop structure.

BRIEF DESCRIPTION OF THE DRAWINGS

The accompanying drawings, together with the specification, illustrate exemplary embodiments of the present invention, and, together with the description, serve to explain the principles of the present invention.

DETAILED DESCRIPTION

Figure 1:
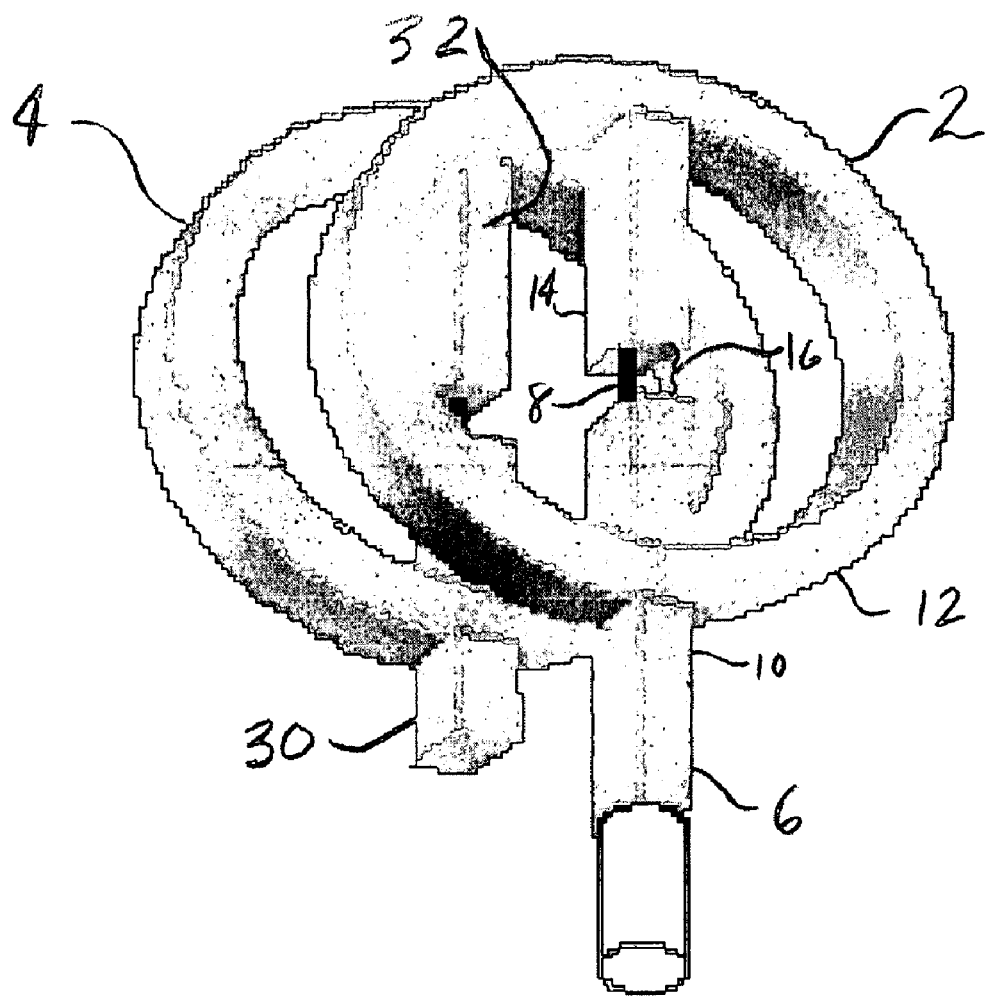
FIG. 1 shows a linearly polarized eddy current sensor according to an embodiment of the present invention.

In the following detailed description, only certain exemplary embodiments of the present invention are shown and described, by way of illustration. As those skilled in the art would recognize, the invention may be embodied in many different forms and should not be construed as being limited to the embodiments set forth herein. Also, in the context of the present application, when an element is referred to as being "on" another element, it can be directly on the another element or be indirectly on the another element with one or more intervening elements interposed therebetween. Like reference numerals designate like elements throughout the specification.

Unless specifically noted, it is intended that the words and phrases in the specification and the claims be given the ordinary and accustomed meaning to those of ordinary skill in the applicable arts. If any other special meaning is intended for any word or phrase, the specification will clearly state and define the special meaning. In particular, most words have a generic meaning. If it is intended to limit or otherwise narrow the generic meaning, specific descriptive adjectives will be used to do so. Absent the use of special adjectives, it is intended that the terms in this specification and claims be given their broadest possible, generic meaning.

Likewise, the use of the words "function" or "means" in the Description of the Invention is not intended to indicate a desire to invoke the special provisions of 35 U.S.C. 112, Paragraph 6, to define the invention. To the contrary, if it is intended to invoke the provisions of 35 U.S.C. 112, Paragraph 6, to define the inventions, the claims will specifically recite the phrases "means for" or "step for" and a function, without also reciting in such phrases any structure, material or act in support of the function. Even when the claims recite a "means for" or "step for" performing a function, if they also recite any structure, material or acts in support of that means or step, then the intention is not to provoke the provisions of 35 U.S.C. 112, Paragraph 6. Moreover, even if the provisions of 35 U.S.C. 112, Paragraph 6 are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Various embodiments of the eddy current sensors described herein induce linearly polarized electric fields on a sample under measurement using alternating magnetic fields from a magnetic quadrupole, and detect the current thus induced in the sheet through electromagnetic induction effects mediated by those same magnetic fields, thus enabling non-contact, non-destructive measurement of properties of the sample in the microwave range.

Because the current and voltage in the circuit that includes the sample are induced and measured through alternating magnetic fields, an aspect of embodiments of the present invention is that the procedure involves no electrodes in contact with the sample, and the requirement of the prior art for forcing a flux path to go from one electrode to another electrode through the sample, is removed.

Another aspect of an embodiment of the present invention is that it may be used on a production line for producing sheet goods by coating the top surface of a box containing an eddy current sensor with a thin Teflon (PTFE) layer that allows the rapidly moving material to slide over the sensor in intimate contact with the sensor without damaging the sensor or the material.

According to various embodiments of the present invention, center frequencies of the sensors can be between approximately 10 MHz up to several GHz. However, other materials, geometries and designs can also be used to achieve other design center frequencies.

FIG. 1 illustrates a resonant linearly polarized eddy current sensor according to an exemplary embodiment of the present invention, including a resonant device 2 and a parasitic device 4 electromagnetically coupled to one another. The resonant device 2 includes a transmission line 6 with an inner conductor 8 and an outer conductor 10 surrounding the inner conductor 8. In the illustrated embodiment, the transmission line 6 is a coaxial cable, but the invention is not limited thereto. The resonant device 2 further includes a loop conductor 12 and a bar conductor 14 extending inside the loop conductor 12 toward the center thereof. The transmission line 6 crosses one side of the loop conductor 12 opposite to the bar conductor 14, extending inside the loop conductor 12. The outer conductor 10 of the transmission line 6 ends without contacting the bar conductor 14, leaving a gap 16 at the center of the loop conductor 12. At the location where the transmission line 6 crosses the loop conductor 12, the outer conductor 10 is in electrical contact with the loop conductor 12, but the inner conductor 8 does not contact the loop conductor 12 at this location. The inner conductor 8 extends through the gap 16, contacting the bar conductor 14 at the opposite end of the gap 16.

Figure 2:
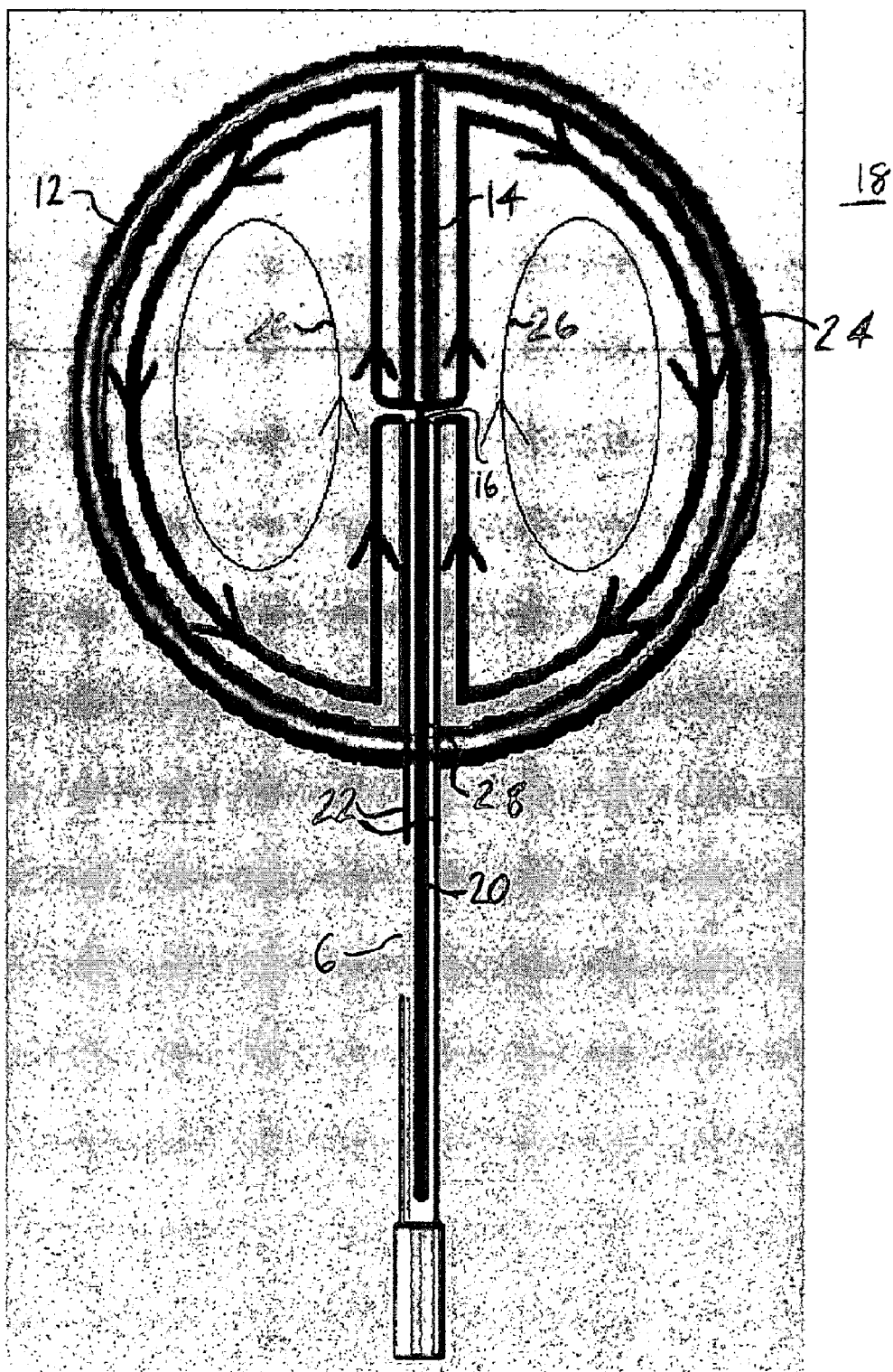
FIG. 2 shows a plan view of a source antenna according to an embodiment of the present invention.

FIG. 2 illustrates a source antenna 18 having a similar construction as the resonant device 2, in a plan view for illustrating a signal path, with instantaneous currents illustrated by arrows. With this construction, a driving signal driven from an external circuit into the transmission line 6 creates a forward current 20 traveling into the source antenna 18 along the inner conductor 8, and a return current 22 traveling out of the source antenna 18 along the outer conductor 10. The forward current 20 in the inner conductor 8 continues forward through the gap 16, along the bar conductor 14, and splits at the junction between the bar conductor 14 and the loop conductor 12, traveling downward in the illustration toward the junction between the transmission line 6 and the loop conductor 12. The current then travels upward in the illustration along the outer conductor 10, to return back through the transmission line 6 to the external circuit. Thus, the driving signal creates two symmetrical D-shaped loops 24 of current of opposite handedness, yielding a magnetic quadrupole.

When the driving signal is an AC signal, the magnetic fields determined by the driving signal oscillate, and by electromagnetic induction, the time-varying magnetic fields induce dynamic, circulating electric fields 26 in space. These fields are strongest over the transmission line 6 and bar conductor 14, and possess a strong component aligned in the direction of these conductors. This is the direction of polarization.

At high enough frequencies, the electromagnetic field will travel as a transmission line wave along the source antenna 18. When this wave hits the short circuit 28 between the loop conductor 12 and the outer conductor 10 of the transmission line 6 at the base of the source antenna 18, it is reflected. As a result, when the total distance traveled from the gap 16 to the short circuit 28 is a fourth of a wavelength, the source antenna 18 will undergo a self-resonance. By placing the gap 16 at the center of the source antenna 18, the distance to the short circuit 28 is minimized and this self-resonance is pushed to as high a frequency as possible.

Figure 3:
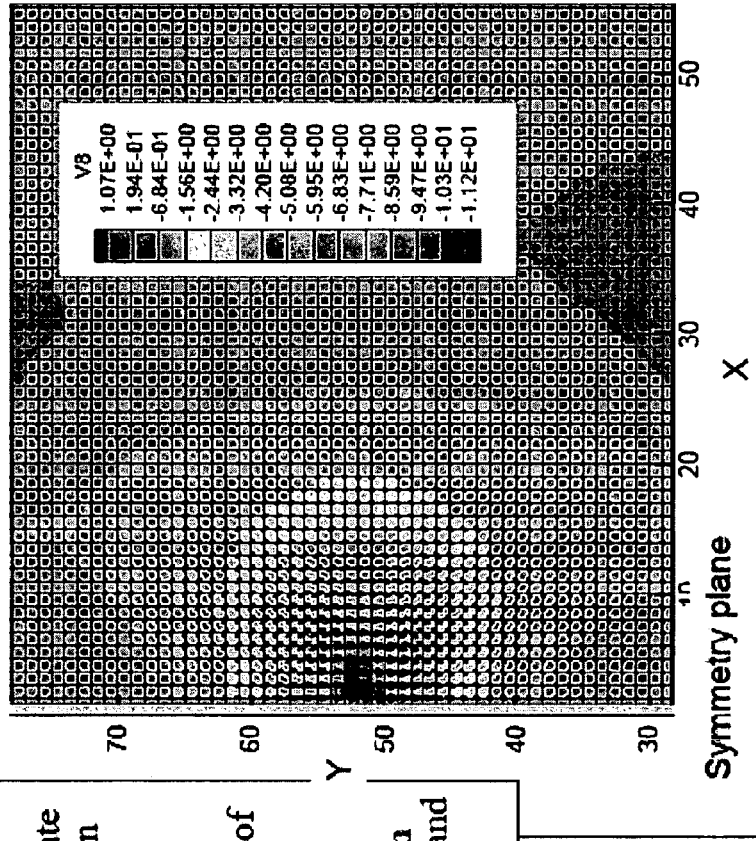
FIG. 3 is a graph showing an electric field in a region above a linearly polarized eddy current sensor according to one embodiment of the present invention.
Figure 4:
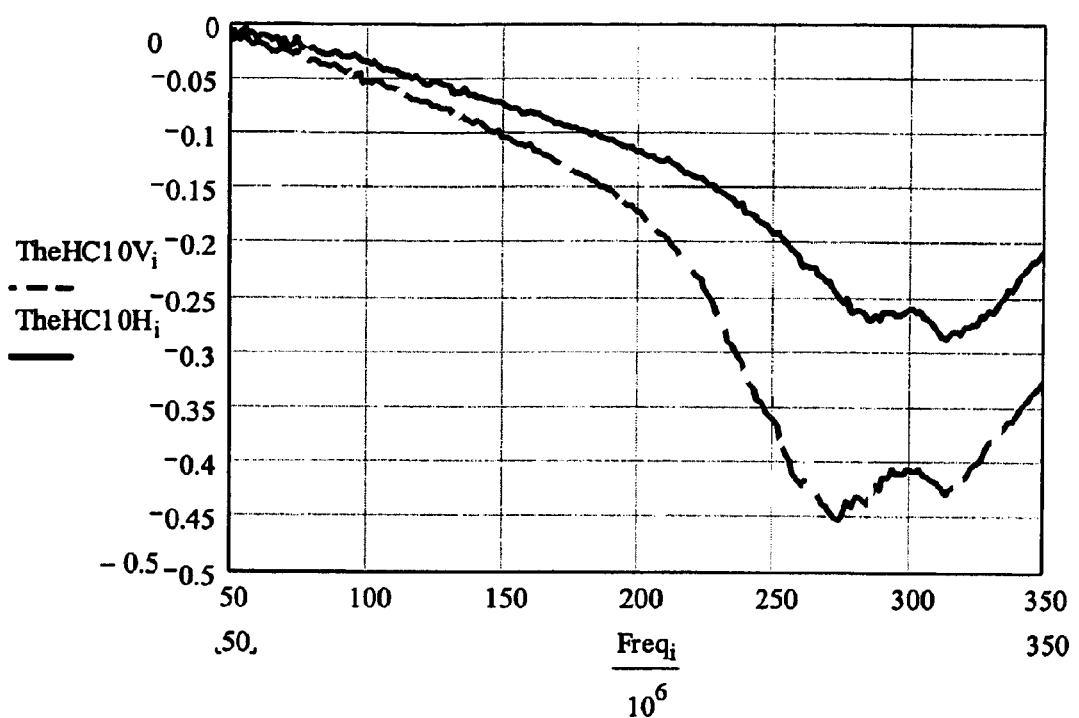
FIG. 4 is a graph showing the sheet impedance of an anisotropic sample in the horizontal direction and the vertical direction as a function of frequency, measured using a source antenna according to one embodiment of the present invention.

FIG. 3 shows half (by symmetry) of a hot-spot of the source antenna 18. The contours are contours of the electric field in the principal direction of polarization, nevertheless the arrows are scaled correctly so one can see the flow field in the hot spot and see there is some component of the electric field perpendicular to the principal direction of polarization in front and behind the spot; but in the spot the field is substantially all in the principal direction.

Because the electric fields induced by the source antenna 18 are substantially polarized, when a resistive material is placed in the proximity of the electric fields, currents induced by the source antenna 18 on a resistive material have a similar polarization. The result is that the self-impedance of the source antenna 18 in the presence of resistive materials is sensitive to any electrical anisotropy of those materials. This is easily proven by placing a ribbon of honeycomb (a typically anisotropic resistive composite material) in the immediate proximity of the source antenna 18. As shown in FIG. 3 for an exemplary embodiment of the present invention, a ribbon of honeycomb measured by other means to possess a 1.5:1 anisotropy at X-Band, exhibits the same anisotropy when measured as a resistive load on the loop.

To generate the data for FIG. 3, the input reflection coefficient (S11) of a source antenna (not coupled to a parasitic device) was calibrated to be the baseline (i.e., 0 dB), and then the change in S11 was detected as a result of a "T-slice" of honeycomb material being placed in contact with the loop. The red curve represents the change in S11 when the polarization direction of the electric field is aligned with the Honeycomb ribbon direction, and the blue curve represents the change in S11 when the polarization direction of the electric field is perpendicular to the ribbon direction. The vertical axis represents dB.

Referring again to FIG. 1, a resonant linearly polarized eddy current sensor according to an embodiment of the present invention can be made by electromagnetically coupling a source antenna 18 to another antenna of a similar construction. When coupled together, the source antenna 18 can be called the resonant device 2, and the second antenna can be called the parasitic device 4. The parasitic device 4 is left open circuited at its input. The resulting coupled resonant-parasitic device combination has a sharp resonance when the diameter of the loop conductor 12 is approximately one twentieth of a wavelength of the driving signal. This resonance frequency can be altered by changing the length of the open circuited feed line 30 of the parasitic device 4, or by changing the physical dimensions of the loops. The sharpness of the resonance and its sensitivity to near-field perturbation can be adjusted by controlling the distance between the resonant device 2 and the parasitic device 4. In one embodiment, the loop to loop distance is about 0.25".

In another embodiment of the invention including a resonant device 2 electromagnetically coupled to a parasitic device 4, the resonance frequency of the parasitic device 4 can be tuned by loading its open circuited feed line with a capacitive impedance. Thus, in an embodiment of the invention where the open circuited feed line 30 is very short (essentially no transmission line is used and all we have is a gapped round symmetric folded dipole), then the resonance is at its maximum (highest frequency). If the open circuited feed line 30 is the length of the bar conductor 32 of the parasitic device 4, the "nominal" resonance frequency results, and if it is made longer or loaded with a capacitor, the resonance frequency is depressed further. With nominal frequency of 240 MHz a device according to an embodiment of the present invention can be tuned as low as 90 MHz simply by lengthening the open circuited feed line 30. It is not recommended that a device be made to resonate at extremely low frequencies compared to its nominal frequency, because then a significant portion of its energy at resonance is stored inside the open circuited feed line 30 and is not available to interact with the near material to sense its properties, thus reducing the efficiency of the device.

The basic principle of inducing currents on a target object and detecting those currents by their reaction on the source or on an auxiliary sensor is generally the principle of operation used by induction metal detectors. However, unlike induction metal detectors known in the prior art, which are generally only able to detect highly conductive objects (metals) with surface resistance on the order of thousandths to millionths of an ohm, various embodiments of the present invention are capable of measuring surface resistances in the range of 10,000 ohms or more.

In one embodiment of the present invention, the sensitivity of the eddy current sensor to material properties of the sheet can be tuned by varying the distance between the resonant device 2 and the parasitic device 4. If very lossy, high conductivity sheets (with sheet resistance values in the range approximately between 300 ohms per square to 5000 ohms per square) are to be measured, then the parasitic device should be close to the resonant device to tighten its coupling to the feeding magnetic field so that the sheet does not completely detune the eddy current sensor. However, if the sheet to be measured has very low conductivity, with sheet resistance values in the range approximately between 10,000 ohms per square to 200,000 ohms per square, then the parasitic device should be separated farther from the resonant device to increase the quality factor Q of the resonance and therefore the sensitivity of the eddy current sensor. Typical separation distances are in the range between approximately 0.05 and 0.25 inches. However, other separation differences that allow properties of a material to be measured can also be used.

Figure 5:
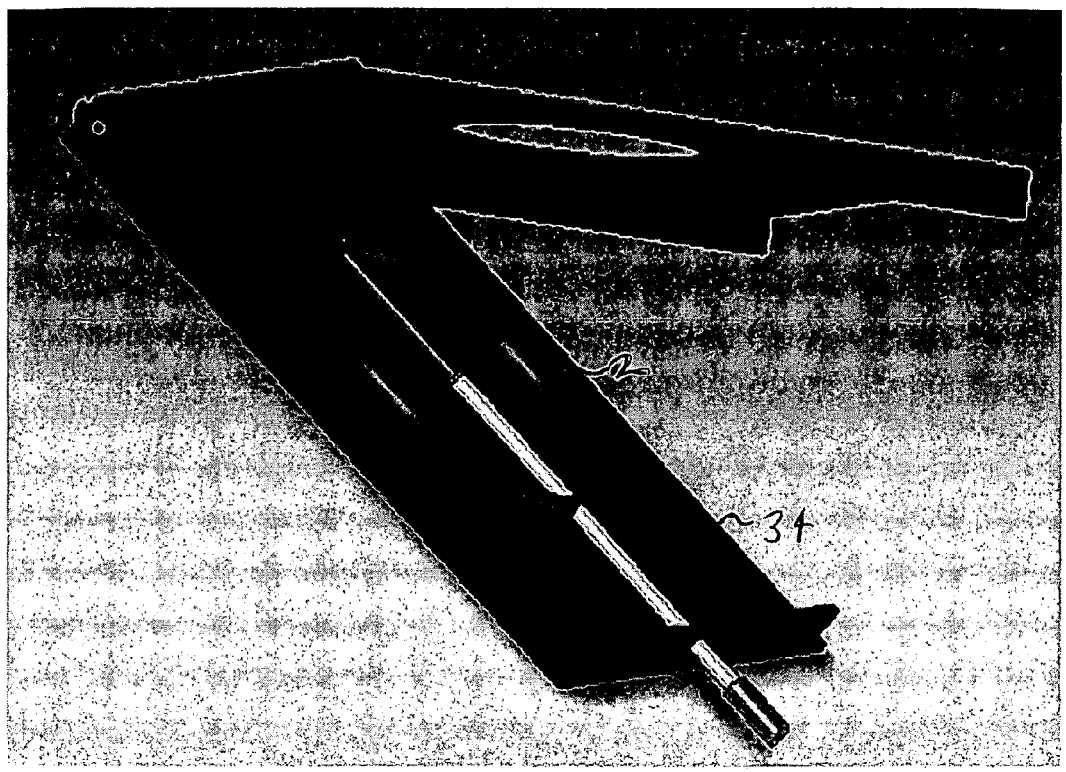
FIG. 5 shows a source antenna placed in a box enclosure according to one embodiment of the present invention.
Figure 6A:
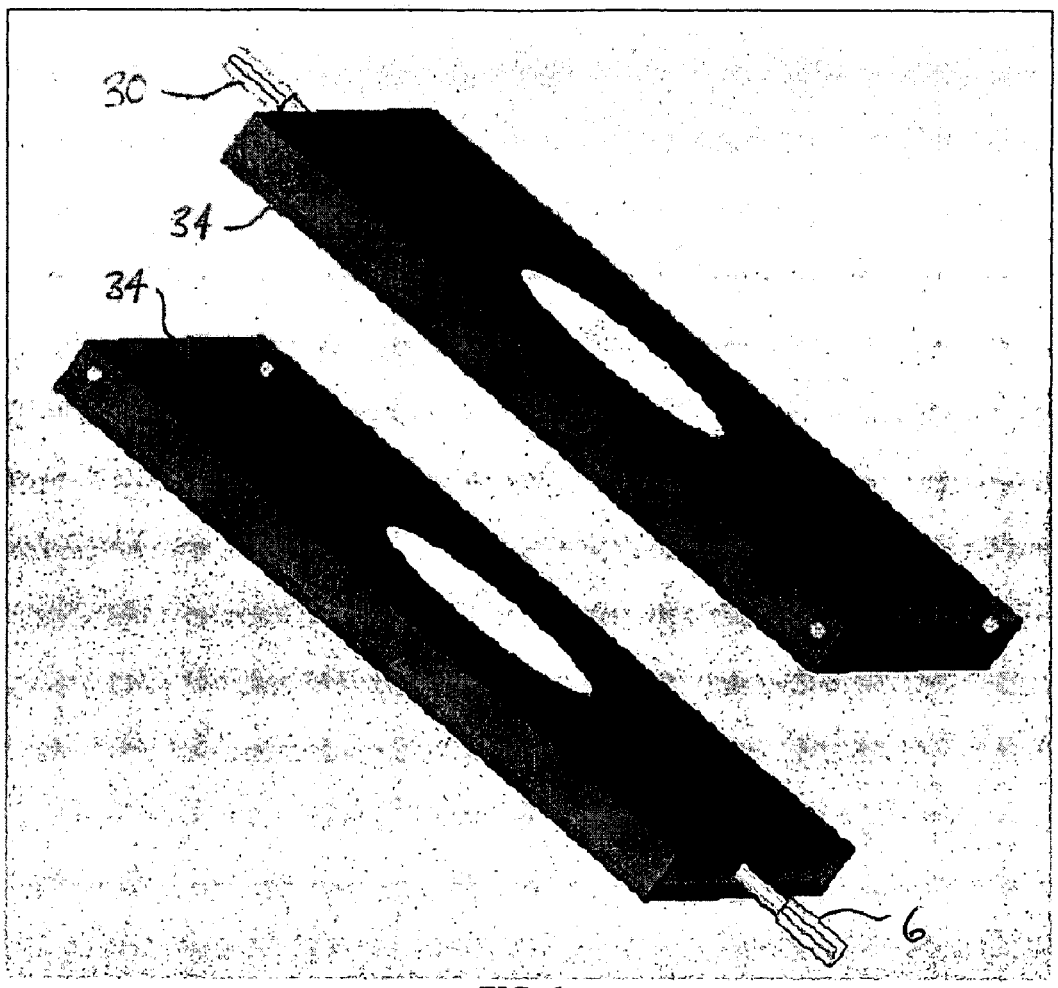
FIGS. 6a and 6b show a source antenna and a parasitic antenna enclosed in box enclosures according to one embodiment of the present invention.
Figure 6B:
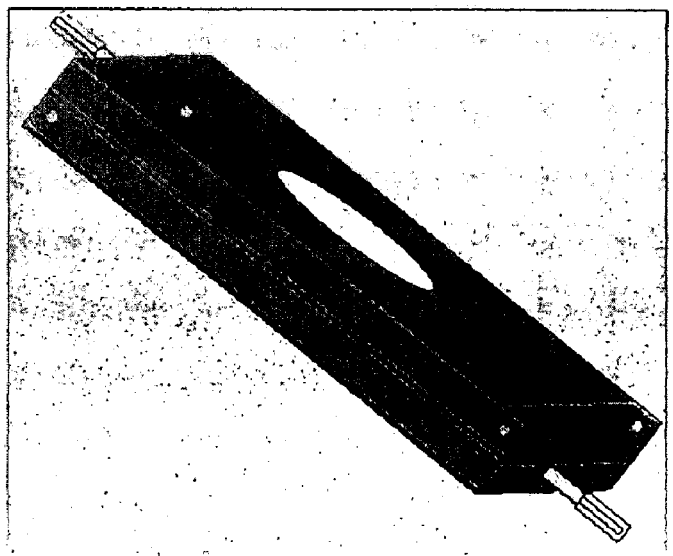

FIGS. 5-6 show an embodiment of the present invention including a resonant device 2 and a parasitic device 4 each enclosed in its own box enclosure 34. According to this embodiment, the distance between the resonant device 2 and the parasitic device 4 is easily controlled. Furthermore, a top surface of the box 34 can be coated with a thin Teflon (PTFE) layer, which allows material being measured to rapidly slide over the sensor in intimate contact with it without damaging the sensor or the material.

Figure 8:
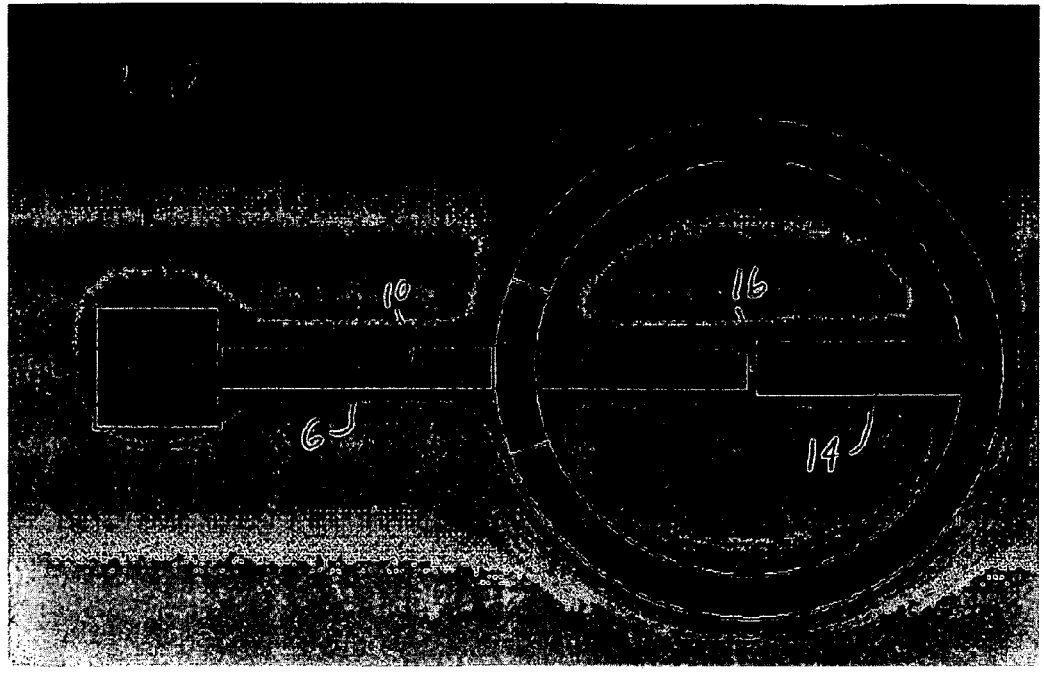
FIGS. 8 and 9 show copper patterns from printed circuit board (PCB) layouts of source antennas according to embodiments of the present invention.
Figure 9:
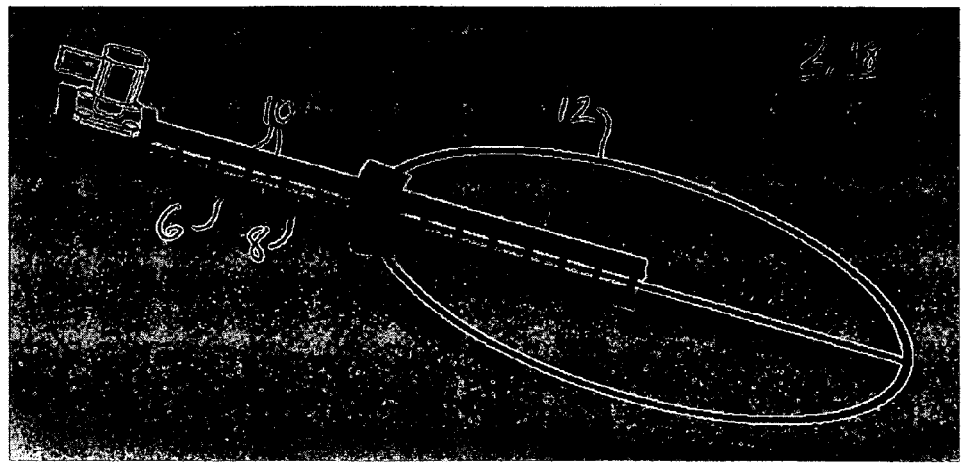

FIGS. 8-9 show copper patterns for printed circuit board (PCB) layouts for two embodiments of a source antenna, indicating that the present invention is not limited to those embodiments described above.

Because the magnetic fields of quadrupoles drop in intensity with distance, r, as $1/r^4$ instead of as $1/r^3$ (as dipole fields do), an embodiment of the sensor may be extremely sensitive to changes very close to it, but relatively insensitive to changes farther away. In a further embodiment, the linearly polarized eddy current sensor may be a useful adjunct to a conventional metal detector device because it can effectively discriminate ellipsoidal targets according to their aspect ratio and the orientation of said target relative to the linearly polarized field the sensor creates. Furthermore, the difference in field intensity change with distance between a dipole and a quadrupole source means that operating in conjunction with a dipole sensor, the quadrupole sensor can help determine the range to a given target by simply comparing the strengths of the signals received by each instrument.

According to an embodiment of a method for measuring surface impedance of a sample, when using the linearly polarized eddy current sensor, the input reflection coefficient S11 of the resonant device 2 can be recorded and normalized (for instance, by using the "math divide" option of a vector network analyzer), so that a baseline 0 dB and 0 degree level can be established. Bringing an impedance sheet into the immediate proximity of the parasitic device alters the resonance of the eddy current sensor. The resulting changes in the amplitude and phase of the input reflection coefficient S11 are proportional to the real and imaginary parts of the sheet Impedance at the resonant frequency. The results for a coupled loop pair tuned to 240 MHz are shown in FIG. 7.

First, the sheet resistance of four different types of sheet materials were tested by some other means at approximately 240 MHz, and then the same materials were tested using a linearly polarized eddy current sensor according to one embodiment of the present invention tuned to 240 MHz. In both graphs of FIG. 7, the horizontal axis shows, on a logarithmic scale, the sheet resistance of the materials measured by the other means. The vertical axis of the top graph shows the change in amplitude of the input reflection coefficient S11 of the linearly polarized eddy current sensor, and the vertical axis of the bottom graph shows the change in phase of S11, with the materials in the immediate proximity of the linearly polarized eddy current sensor.

Figure 7:
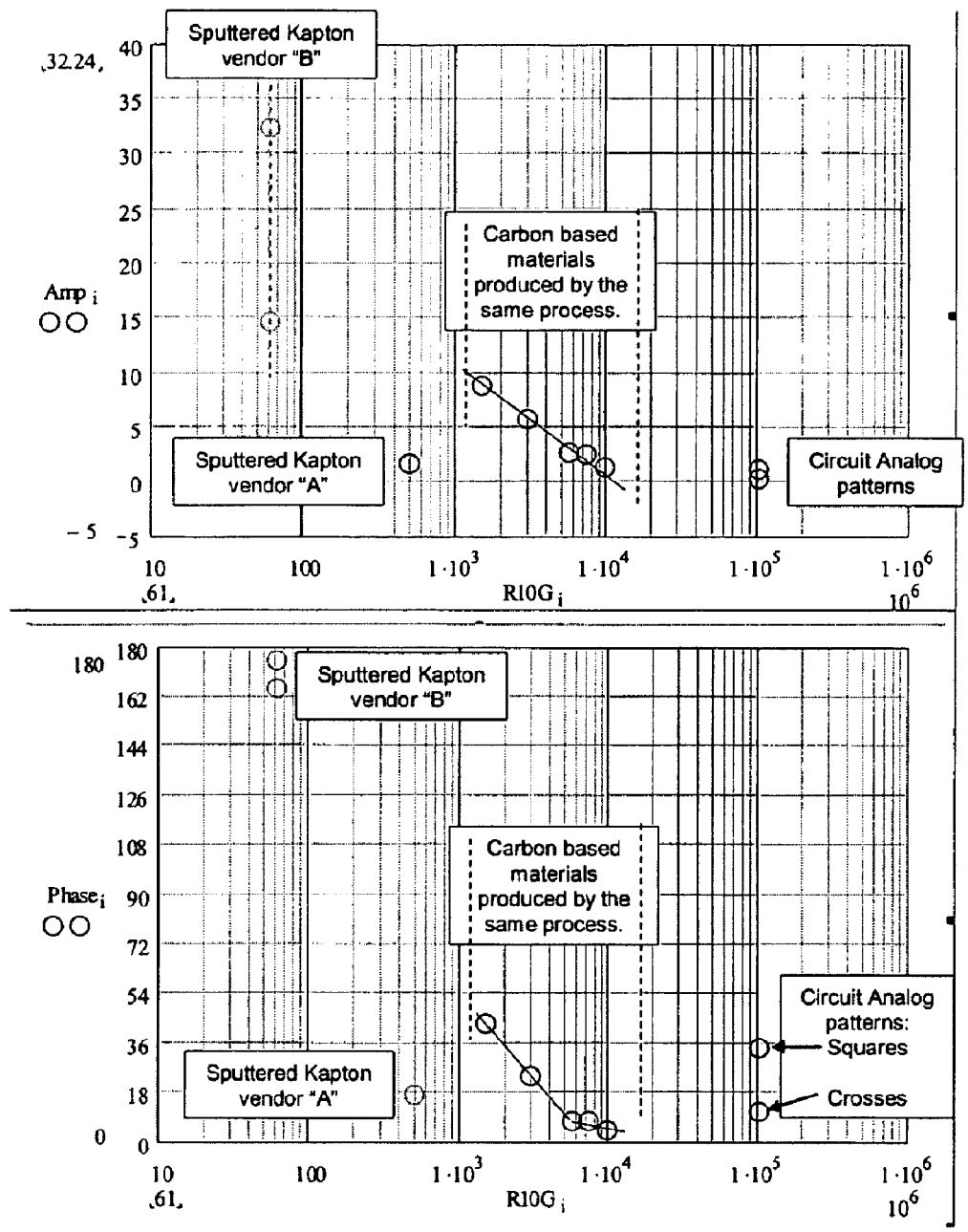
FIG. 7 shows a graph of changes in amplitude and phase of an input reflection coefficient (S11) of a resonant linearly polarized eddy current sensor according to one embodiment of the present invention, when measuring several different samples.

The central portions of FIG. 7 show a series of carbon-loaded sheets produced using a uniform coating process. The top graph demonstrates a characteristic linear correlation between the measured value and the amplitude response of the eddy current sensor. The very high resistance values (towards the right) start to deviate from the linear relationship. The explanation can be seen in the phase response in the bottom graph, where the deviation of the same sheets is greater, exhibiting a larger phase shift than would be predicted by a linear relationship. This indicates that the carbon coating is starting to become disconnected at these loading levels, thus increasing the series capacitive reactance of the material. Two sputtered R films are also included in the data, one of which exhibited significant anisotropy. Finally a couple of Circuit Analog (CA) resistive patterns are also included, although their position on the horizontal axis has been chosen arbitrarily. It is clear that a CA pattern can exhibit low loss at these frequencies yet have very high capacitive reactance (high phase shift).

Referring now back to FIGS. 2, 5, 8, and 9, an embodiment of the present invention provides an eddy current sensor including a source antenna 18 including two sub-loops 24 substantially symmetrical with respect to an imaginary line between the two sub-loops 24, wherein the source antenna 18 is adapted to generate a magnetic quadrupole when electric currents circulate on the two sub-loops 24 in opposing directions. The source antenna 18 is adapted to induce a substantially linearly polarized electric field in a region between the two sub-loops.

Referring now back to FIG. 1, the eddy current sensor may further include a parasitic device 4 coupled to the source antenna 18. When part of the coupled combination of source antenna 18 and parasitic device 4, the source antenna 18 may also be referred to as the resonant device 2. An embodiment of the parasitic device 4 may further include a second two sub-loops substantially symmetrical with respect to a second imaginary line between the second two sub-loops.

Referring now back to FIGS. 2, 5, 8, and 9, an embodiment of the source antenna 18 may further include a first transmission line 6 for communicating with an external circuit. The source antenna 18 may further include a first loop conductor 12, bisected by a first imaginary line crossing the first loop conductor 12 at a first point and a second point, such that a first part and a second part of the loop conductor on a first side and a second side of the first imaginary line comprise at least part of a first sub-loop and a second sub-loop, respectively, among the two sub-loops 24. The first transmission line 6 may include a first conductor 10 and a second conductor 8. The first transmission line 6 may cross the first point such that the first conductor 10 is electrically coupled with the first loop conductor 12 at about the first point. The first conductor 10 may extend toward an inside of the first loop conductor 12 along the first imaginary line, ending at a third point, on the first imaginary line. The second conductor may extend along the first imaginary line beyond the third point, to be electrically coupled with the first loop conductor 12 at the second point.

In a further embodiment of the source antenna, the first loop conductor 12 may have an annular shape, and the first transmission line may be a coaxial conductor, wherein the first conductor 10 is an outer conductor of the coaxial conductor, and the second conductor 8 is an inner conductor of the coaxial cable between the first point and the third point. The second conductor 8 may further include a first rod 14 having a cross-section substantially identical to that of the first loop conductor 12, the first rod 14 extending from the second point to a fourth point on the first imaginary line between the second point and the third point, such that there is a gap 16 between an end of the first rod 14 at the fourth point and an end of the first conductor 10 at the third point. A second rod may extend along the first imaginary line through the gap 16 to electrically couple the first rod 14 to the inner conductor 8 of the coaxial cable. The gap 16 may be approximately at the center of the first loop conductor 12.

As mentioned above, referring again to FIG. 1, an embodiment of the current invention may include a parasitic device 4 coupled to the source antenna 18. Again, when coupled to a parasitic device 4, the source antenna 18 may be referred to as a resonant device 2. The parasitic device 4 may have a shape substantially the same as the resonant device 2. The parasitic device may have a transmission line 30 that extends outward from the parasitic device 4, the second transmission line 30 being open circuited, terminating at a distance from an outer portion of the parasitic device 4.

Referring now back to FIGS. 1, 2, 3, 5, 6, 8, and 9, another embodiment of the present invention provides a method of measuring a sheet impedance of a sample. The method includes driving two substantially symmetrical circulating currents circulating in opposing directions on a compound loop structure 18 including two sub-loops 24, to result in a magnetic quadrupole. The method further includes varying a magnetic field of the magnetic quadrupole over time to induce an electric field 26 in a region between the two current loops. The method further includes detecting changes in an electromagnetic field, the changes being caused by currents in the sample driven by the induced electric field 26, wherein the sheet impedance of the sample corresponds to the changes in the electromagnetic field.

The method may further include coupling the compound loop structure 18 with a parasitic compound loop structure 4 to increase a quality factor of the compound loop structure 18. As noted above with respect to the source antenna 18, the compound loop structure 18 may be referred to as a resonant device 2 when coupled to a parasitic compound loop structure 4. The parasitic compound loop structure 4 may include an open circuited transmission line 30, and the method may further include tuning a resonance frequency of the compound loop structure 2, 18 by controlling a length of the open circuited transmission line 30. Controlling a distance between the compound loop structure 2, 18 and the parasitic compound loop structure 4 may be used to control a sensitivity to the changes in the electromagnetic field.

According to a further embodiment, as illustrated in FIG. 3, the induced electric field may be substantially linearly polarized along a first direction in a region of the sample, such that the sheet impedance is a directionally dependent sheet impedance in the first direction. In this case, the method of measuring a sheet impedance of a sample may further include changing an orientation of the sample with respect to the compound loop structure 2, 18 such that the substantially linearly polarized electric field points in a second direction along a surface of the sample. The method may further include measuring the directionally dependent sheet impedance of the sample in the second direction. These data may then be compared to find an electrical anisotropy of the sample.

Another embodiment of the present invention provides a method of measuring frequency dependent, direction-dependent sheet impedance of a sample using an eddy current sensor comprising a source antenna 2, 18 and a parasitic antenna 4, the method including inducing an electric field that is linearly polarized along a first direction, on a part of the sample, by driving two AC current loops 24 in opposing directions on the source antenna 2, 18 at a resonant frequency of the eddy current sensor to generate a magnetic quadrupole comprising a time-varying magnetic field. The method may further include sensing a current in the sample, the current driven by the induced linearly polarized electric field, by measuring changes in an amplitude and a phase of an input reflection coefficient S11 of the eddy current sensor. According to this embodiment, the sheet impedance at the frequency and in the direction of polarization corresponds to the changes in the amplitude and the phase of the input reflection coefficient S11.

Various embodiments of the eddy current sensors described herein induce linearly polarized electric fields on a sample under measurement using alternating magnetic fields from a magnetic quadrupole, and detect the current thus induced in the sheet through electromagnetic induction effects mediated by those same magnetic fields, thus enabling non-contact, non-destructive measurement of properties of the sample in the microwave range.

In view of the foregoing, an embodiment of the present invention provides a sensor capable of quickly measuring surface impedance characteristics of a sample without requiring destruction of or contact with the sample. In one embodiment, because the current and voltage in the circuit that includes the sample are induced and measured through alternating magnetic fields, an embodiment involves no electrodes in contact with the sample, and the requirement of the prior art for forcing a flux path to go from one electrode to another electrode through the sample, is removed.

An embodiment of the present invention may be used on a production line for producing sheet goods by coating the top surface of a box containing an eddy current sensor with a thin Teflon (PTFE) layer that allows the rapidly moving material to slide over the sensor in intimate contact with the sensor without damaging the sensor or the material. In an equivalent embodiment, the rapidly moving material is maintained at a fixed small distance from the surface of the sensor by a proper arrangement of idler cylinders thus bringing the material within the region of induced linearly polarized field without actually making contact with the surface of the sensor.

Also, in certain embodiments of the present invention as described above, center frequencies of the sensors can be between approximately 10 MHz up to several GHz. However, other materials, geometries and designs can also be used to achieve other design center frequencies.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. An eddy current sensor comprising:
   a source antenna comprising two sub-loops substantially symmetrical with respect to an imaginary line between the two sub-loops; and
   a first transmission line for communicating with an external circuit,
   wherein the source antenna is adapted to generate a magnetic quadrupole when electric currents circulate on the two sub-loops in opposing directions,
   wherein the source antenna is adapted to induce a substantially linearly polarized electric field in a region between the two sub-loops,
   wherein the source antenna further comprises a first loop conductor, bisected by a first imaginary line crossing the first loop conductor at a first point and a second point, such that a first part and a second part of the loop conductor on a first side and a second side of the first imaginary line comprise at least part of a first sub-loop and a second sub-loop, respectively, among the two sub-loops, wherein the first transmission line comprises a first conductor and a second conductor, and wherein the first transmission line crosses the first point such that the first conductor is electrically coupled with the first loop conductor at about the first point; and wherein the first conductor extends toward an inside of the first loop conductor along the first imaginary line and ends at a third point, on the first imaginary line, and the second conductor extends along the first imaginary line beyond the third point, to be electrically coupled with the first loop conductor at the second point.

2. The eddy current sensor according to claim 1, wherein the first loop conductor has an annular shape, and wherein the first transmission line comprises a coaxial conductor, wherein:
the first conductor comprises an outer conductor of the coaxial conductor, and
the second conductor comprises an inner conductor of the coaxial cable between the first point and the third point.

3. The eddy current sensor according to claim 2, wherein the second conductor further comprises:
a first rod having a cross-section substantially identical to that of the first loop conductor, the first rod extending from the second point to a fourth point on the first imaginary line between the second point and the third point, such that there is a gap between an end of the first rod at the fourth point and an end of the first conductor at the third point, and
a second rod extending along the first imaginary line through the gap to electrically couple the first rod to the inner conductor of the coaxial cable.

4. The eddy current sensor according to claim 2, wherein the gap is approximately at the center of the first loop conductor.

5. The eddy current sensor according to claim 1, further comprising a parasitic device coupled to the source antenna.

6. The eddy current sensor according to claim 5, wherein the parasitic device further comprises:
a second loop conductor and a second transmission line, configured to form a second two sub-loops substantially symmetrical with respect to a second imaginary line between the two sub-loops,
wherein the second transmission line extends outward from the second loop conductor, the second transmission line being open circuited, terminating at a distance from an outer portion of the second loop conductor.

7. The eddy current sensor according to claim 5, wherein the parasitic device is a resonant device having a tunable frequency.

8. The eddy current sensor according to claim 5, wherein a distance between the parasitic device and the source antenna is adjustable.

9. The eddy current sensor according to claim 1, wherein the eddy current sensor is operable to assess sheet impedance of sheet goods having a sheet impedance of at least 10,000 ohms per square and up to 200,000 ohms per square.

10. The eddy current sensor according to claim 1, wherein a center frequency of the eddy current sensor is at least 10 MHz.

11. The eddy current sensor according to claim 1, wherein the two sub-loops define a loop conductor, and further comprising a bar conductor extending inside the loop conductor toward the center thereof.

12. A method of measuring a sheet impedance of a sample, the method comprising:

driving two substantially symmetrical circulating currents circulating in opposing directions on a compound loop structure comprising two sub-loops, to result in a magnetic quadrupole, varying a magnetic field of the magnetic quadrupole over time to induce an electric field in a region between the two current loops; and detecting changes in an electromagnetic field, the changes being caused by currents in the sample driven by the induced electric field, wherein the two sub-loops are substantially symmetrical with respect to an imaginary line between the two sub-loops;

wherein the compound loop structure is adapted to induce a substantially linearly polarized electric field in a region between the two sub-loops, wherein the compound loop structure further comprises a first loop conductor, bisected by a first imaginary line crossing the first loop conductor at a first point and a second point, such that a first part and a second part of the loop conductor on a first side and a second side of the first imaginary line comprise at least part of a first sub-loop and a second sub-loop, respectively, among the two sub-loops, wherein a first transmission line for communicating with an external circuit and comprising a first conductor and a second conductor crosses the first point such that the first conductor is electrically coupled with the first loop conductor at about the first point; and wherein the first conductor extends toward an inside of the first loop conductor along the first imaginary line and ends at a third point, on the first imaginary line, and the second conductor extends along the first imaginary line beyond the third point, to be electrically coupled with the first loop conductor at the second point, and wherein the sheet impedance of the sample corresponds to the changes in the electromagnetic field.

13. The method of measuring a sheet impedance of a sample according to claim 12, further comprising coupling the compound loop structure with a parasitic compound loop structure to increase a quality factor of the compound loop structure.

14. The method of measuring a sheet impedance of a sample according to claim 13, wherein the parasitic compound loop structure comprises an open circuited transmission line, the method further comprising tuning a resonance frequency of the compound loop structure by controlling a length of the open circuited transmission line.

15. The method of measuring a sheet impedance of a sample according to claim 13, further comprising controlling a distance between the compound loop structure and the parasitic compound loop structure to control a sensitivity to the changes in the electromagnetic field.

16. The method of measuring a sheet impedance of a sample according to claim 12, wherein the sheet impedance of the sample is at least 300 ohms per square.

17. The method of measuring a sheet impedance of a sample according to claim 16, wherein the sheet impedance of the sample is at least 10,000 ohms per square.

18. The method of measuring a sheet impedance of a sample according to claim 13, wherein the parasitic compound loop structure is a resonant device having a tunable frequency.

19. The method of measuring a sheet impedance of a sample according to claim 12, wherein the induced electric field is substantially linearly polarized along a first direction in a region of the sample, such that the sheet impedance is a directionally dependent sheet impedance in the first direction.

20. The method of measuring a sheet impedance of a sample according to claim 19, further comprising: changing an orientation of the sample with respect to the compound loop structure such that the substantially linearly polarized electric field points in a second direction along a surface of the sample, and measuring the directionally dependent sheet impedance of the sample in the second direction.

21. The method of measuring a sheet impedance of a sample according to claim 20, further comprising comparing the sheet impedance in the first direction and the sheet impedance in the second direction to find an electrical anisotropy of the sample.

22. A method of measuring frequency-dependent, direction-dependent sheet impedance of a sample using an eddy current sensor comprising a source antenna and a parasitic antenna, the method comprising:
    inducing an electric field that is linearly polarized along a first direction, on a part of the sample, by driving two AC current loops in opposing directions on two sub-loops of the source antenna at a resonant frequency of the eddy current sensor to generate a magnetic quadrupole comprising a time-varying magnetic field;
    establishing a resonant frequency of the parasitic antenna;
    sensing a current in the sample, the current driven by the induced linearly polarized electric field, by measuring changes in an amplitude and a phase of an input reflection coefficient of the eddy current sensor,
    wherein the two sub-loops are substantially symmetrical with respect to an imaginary line between the two sub-loops;
    wherein the source antenna is adapted to induce a substantially linearly polarized electric field in a region between the two sub-loops,
    wherein the source antenna further comprises a first loop conductor, bisected by a first imaginary line crossing the first loop conductor at a first point and a second point, such that a first part and a second part of the loop conductor on a first side and a second side of the first imaginary line comprise at least part of a first sub-loop and a second sub-loop, respectively, among the two sub-loops,
    wherein a first transmission line for communicating with an external circuit and comprising a first conductor and a second conductor crosses the first point such that the first conductor is electrically coupled with the first loop conductor at about the first point; and wherein the first conductor extends toward an inside of the first loop conductor along the first imaginary line and ends at a third point, on the first imaginary line, and the second conductor extends along the first imaginary line beyond the third point, to be electrically coupled with the first loop conductor at the second point, and
    wherein the sheet impedance at the frequency and in the direction of polarization corresponds to the changes in the amplitude and the phase of the input reflection coefficient.

23. The method of measuring frequency-dependent, direction-dependent sheet impedance of a sample according to claim 22, wherein the sheet impedance of the sample is at least 300 ohms per square.

24. The method of measuring frequency-dependent, direction-dependent sheet impedance of a sample according to claim 23, wherein the sheet impedance of the sample is at least 10,000 ohms per square.

* * * * *

UNITED STATES PATENT AND TRADEMARK OFFICE
CERTIFICATE OF CORRECTION

| | |
|---|---|
| PATENT NO. | : 8,324,894 B2 |
| APPLICATION NO. | : 12/520809 |
| DATED | : December 4, 2012 |
| INVENTOR(S) | : Rodolfo E. Diaz |

It is certified that error appears in the above-identified patent and that said Letters Patent is hereby corrected as shown below:

Title Page 1, column 1, item (75), (Inventors): line 1, Delete "Phoeniz," and insert -- Phoenix, --, therefor.

Signed and Sealed this
Twenty-sixth Day of March, 2013

Teresa Stanek Rea
*Acting Director of the United States Patent and Trademark Office*